(12) United States Patent     (10) Patent No.:   US 12,698,252 B2

Raone                        (45) Date of Patent:     Aug. 4, 2026

(54) PROCESS FOR EXTRUDING A NON-FERROUS METAL USING A LUBRICANT RELEASE AGENT COMPOSITION

(71) Applicant: BARALDI S.R.L., Castel San Pietro Terme (IT)

(72) Inventor: Cosimo Raone, Castel Guelfo (IT)

(73) Assignee: BARALDI S.R.L., Castel San Pietro Terme (IT)

( * ) Notice: Subject to any disclaimer, the term of this patent is extended or adjusted under 35 U.S.C. 154(b) by 655 days.

(21) Appl. No.: 17/991,362

(22) Filed: Nov. 21, 2022

(65) Prior Publication Data

US 2023/0159431 A1     May 25, 2023

(30) Foreign Application Priority Data

Nov. 23, 2021    (IT) ........................ 102021000029573

(51) Int. Cl.
     *C07C 69/90*       (2006.01)
(52) U.S. Cl.
     CPC .................................... *C07C 69/90* (2013.01)
(58) Field of Classification Search
     CPC ...................................................... C07C 69/70
     See application file for complete search history.

(56) References Cited

U.S. PATENT DOCUMENTS

| | | | | |
|---|---|---|---|---|
| 4,834,891 A | * | 5/1989 | Eguchi | ................. C10M 105/30 |
| | | | | 508/158 |
| 2018/0251699 A1 | * | 9/2018 | Odink | ................. C10M 169/00 |
| 2023/0159431 A1 | * | 5/2023 | Raone | .................... B21C 23/32 |
| | | | | 252/579 |

FOREIGN PATENT DOCUMENTS

| | | | | | |
|---|---|---|---|---|---|
| CA | 2222333 | C | * | 5/2007 | ............. C08G 63/20 |
| CN | 107523386 | A | * | 12/2017 | |
| EP | 4183857 | B1 | * | 1/2025 | ............. B21C 23/32 |
| ES | 3023832 | T3 | * | 6/2025 | ............. B21C 23/32 |
| JP | 2010132871 | A | * | 6/2010 | |

OTHER PUBLICATIONS

CN 107523386 A. An English Translation. (Year: 2017).*
Italian Search Report dated Jul. 7, 2022 from counterpart Italian Patent Application No. 102021000029573.

* cited by examiner

*Primary Examiner* — Mark Eashoo
*Assistant Examiner* — M. Reza Asdjodi
(74) *Attorney, Agent, or Firm* — Silvia Salvadori, P.C.; Silvia Salvadori

(57)             ABSTRACT

Described is the use of a composition in a process for extruding metals. Said composition includes at least one sodium and/or potassium phthalate and optionally at least one phthalate of an alkaline-earth metal.

6 Claims, 1 Drawing Sheet

PROCESS FOR EXTRUDING A NON-FERROUS METAL USING A LUBRICANT RELEASE AGENT COMPOSITION

This application claims priority to Italian Patent Application 102021000029573 filed Nov. 23, 2021, the entirety of which is incorporated by reference herein. This invention relates to the use of a lubricant release agent composition in a process for extruding a metal.

BACKGROUND ART

The extrusion of metal materials is a process by which, by means of a plastic deformation, parts with a constant cross-section are obtained, for example plates, pipes, profiled sections and bars.

The extrusion process is used in industrial production for metal materials such as aluminium, copper, lead and steel. The material which must be processed and transformed is usually in the pasty state, in the form of pallets or powder and is forced by compression into a mould, in order to obtain the desired product, in practice an outer shape to be subsequently used.

The moulding is performed by compression of the metal material, in the form of a billet, through a die designed ad hoc to give the desired shape to the material being processed. It is essential that the metal is in a pasty melting or softening state, so that the plastic formation passage can occur.

Once the metal material has been acquired, for example aluminium, this is brought to the heating oven, which has a temperature of between 440 and 500° C.; the product is then pressed with a piston against a steel die and the extruded material moves along a roller surface, where it is cooled. The final section of the billet, corresponding to some tens of mm (near the piston), since it is as a potential source of imperfections for the profiles and impurities, is not extruded, but cut at the end of the cycle, by means of an automatic shearing device and then recovered by remelting (billet bottom). Due to the high temperature of the billet, the billet metal tends to attach to the piston head of the press and to remain welded to said head and it can lock the piston causing damage to the press.

Various solutions have been introduced to prevent the billet from remaining adhered to the piston head, for example, grease and oil and/or wax-based pastes with or without adding solid pigments such as graphite, aluminium and others are used. However, this type of product requires a manual application with a pad or brush. Due to the high temperature, these products can result in dripping (loss and soiling of the work environment) and invariably give rise to the development of rather dense fumes and vapours. Moreover, said products are combustible and can catch fire.

A second solution relates to the use of a layer of carbon black which, thanks to a short combustion, deposits on the treated surface. However, due to the combustion the use of said product is dangerous and may be harmful if inhaled.

Boron nitride is a synthetic ceramic material which at the working temperatures does not undergo alterations. This product is particularly effective if deposited in such a way as to perfectly cover the entire treated surface. As it is not, in fact, able to migrate on the surface, any areas left uncovered give rise to metallization and gluing between the press heel and the billet. Moreover, the very light powder spreads into the environment and can be inhaled.

Moreover, water-based products, when sprayed on very hot surfaces (>200° C.), are subject to the calefaction phenomenon (or Leidenfrost effect) whereby a vapour barrier forms instantly between sprayed droplets and metal, which prevents direct contact of liquid-metal and the film deposition. The application of these materials inevitably results in incomplete and non-uniform dripping and film, which means that these products fall in a category which is not widespread, although it is still used.

For this reason, there is a strongly felt need to overcome the above-mentioned technical problem, avoiding the above-mentioned drawbacks.

SUMMARY OF THE INVENTION

The invention relates to the use of a composition in a process for extruding metals. Said composition comprises at least one sodium and/or potassium phthalate and optionally at least one phthalate of an alkaline-earth metal.

Preferably, the composition comprises orthophthalate disodium. The composition is preferably in the form of a powder with a grain size of between 5 and 120 μm. According to an embodiment, the composition is applied on at least one surface 101 of a head 100 of a piston 10 of an extrusion press 1 and/or on at least one surface 201 of a metal billet 20. Preferably, the composition is applied before the start of the extrusion process in order to facilitate the detachment of the at least one surface 101 of the head 101 of the piston 10 from the billet 20 at the end of the extrusion process.

DETAILED DESCRIPTION OF THE INVENTION

Figure 1:
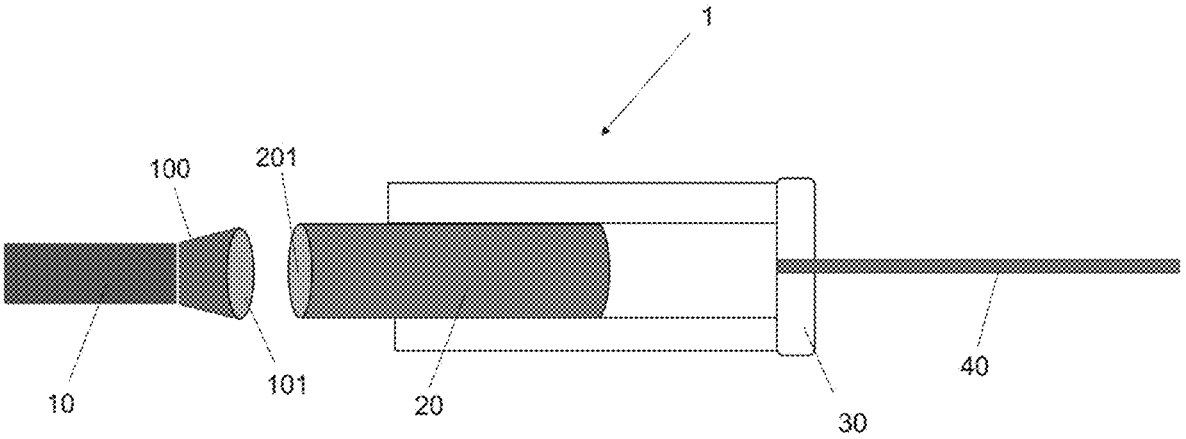
FIG. 1 shows a diagram of a press 1 for the extrusion of a metal.

The invention relates to the use of a composition in a process for extruding metals. Said composition comprises at least one sodium and/or potassium phthalate and optionally at least one phthalate of an alkaline-earth metal.

According to an embodiment, the composition is in the form of powder. Preferably, the composition is in the form of powder with a grain size of between 10 and 150 μm, more preferably between 5 and 120 μm.

According to an embodiment, the sodium phthalate is selected between monosodium phthalate and/or disodium phthalate. Preferably, the disodium phthalate is selected from among disodium orthophthalate, disodium isophthalate and disodium terephthalate. According to a preferred embodiment, the disodium phthalate is orthophthalate disodium.

According to a further embodiment, the potassium phthalate is selected from among monopotassium phthalate or dipotassium phthalate.

Preferably, the phthalate of an alkaline-earth metal is selected from between an orthophthalate calcium or magnesium salt or isophthalate or terephthalate. According to an embodiment, the composition comprises at least one solid pigment, preferably said at least one solid pigment is selected from among: talc, mica, boron or graphite nitride, or other minerals.

According to a preferred embodiment, the composition comprises orthophthalate disodium optionally in a mixture with at least one phthalate of an alkaline-earth metal.

According to an embodiment, the composition comprises the sodium or potassium phthalate in a concentration of between 20 and 75% weight/weight, preferably between 30 and 60% w/w.

According to an embodiment, the composition comprises at least a phthalate of an alkaline-earth metal in a concentration of between 20 and 75% weight/weight, preferably between 30 and 60% w/w.

According to a preferred embodiment, the composition consists of disodium phthalate.

According to an embodiment, the composition is applied on at least one surface 101 of a head 100 of a piston 10 of an extrusion press 1 and/or on at least one surface 201 of a metal billet 20. Preferably, the composition is applied before the start of the extrusion process in order to facilitate the detachment of the surface 101 of the head 101 of the piston 10 from the billet 20 at the end of the extrusion process. Preferably, the extrusion process is a process for extruding a non-ferrous metal, more preferably made of aluminium or copper or alloys thereof with other metals.

According to an embodiment, the composition is applied on the at least one surface 101 of the head 100 of the piston 10 of the press 1 and/or on the at least one surface 201 of the metal billet 20 with systems and methods known to an expert in the trade. Preferably, the composition is applied by means of a spray, preferably using an electrostatic type spray system.

The Applicant has surprisingly found that the composition according to the invention is able to prevent the metal of the billet 20 from sticking to the head 100 of the piston 10 or remaining welded thereto and, therefore, the piston 10 remaining locked, or creating damage due to breakage of the tools of the press 1 when retracting. The composition can be therefore be defined as a lubricant release agent.

The composition according to the invention has a melting point of between 400 and 450° C., slightly less than or equal to the extrusion process temperatures. For this reason, after its application on the at least one surface 101 of the head 100 of the piston 10 of the press 1 and/or on the at least one surface 201 of the metal billet 20 it starts to melt thanks to the high temperature of the billet 20 or the head 100 of the piston 10 and to spread spontaneously on the treated surface. The subsequent compression between the head 100 of the piston 10 and the billet 20 leads to the complete stretching of a film which covers the entire surface in contact forming a complete and continuous barrier film.

Moreover, the use of the composition according to invention reduces the consumption with respect to boron nitride, since the product does not create static accumulations of powder, but always covers the surface regardless of how small the quantity applied.

In order to reduce the consumption of the costly boron nitride as much as possible, a grain size of between 2 and 30 microns is used with an average value of around 10 microns, such as to guarantee a covering capacity of 5-15 $m^2/g$. The composition according to the invention comprises sodium or potassium phthalate with a much greater grain size, of between 20 and 100 microns, due to the melting property which increases the covering capacity. This means that during the spray dispensing the boron nitride tends to spread in the surrounding space more intensely and rapidly compared to sodium or potassium phthalate, which, on the other hand, reaches the surface to be treated due to the electrostatic charge, without further spreading into the air. In this way, the composition spreads very little outside the treated surfaces, avoiding affecting the press 1, the peripherals of the press and the surrounding environments. Above all, the extent of the amount inhaled by the operators present in the proximity of the machine is lower. Lastly, this reduces defects due to inclusions and streaks of the profiled sections 40 obtained with the composition according to the invention.

The invention claimed is:

1. A process for extruding a non-ferrous metal, consisting of:

providing a composition consisting of at least one of sodium or potassium phthalate, and optionally at least one phthalate of an alkaline-earth metal, applying said composition on at least one surface of a head of a piston of an extrusion press and/or on at least one surface of a metal billet before starting said extruding process, wherein said composition prevents the metal billet from sticking to the head of the piston of the extrusion press, and wherein said composition is a release agent composition, and wherein said release agent composition is in powder form.

2. The process according to claim 1, wherein the release agent composition has a grain size of between 10 and 150 μm.

3. The process according to claim 2, wherein the release agent composition has a grain seize of between 5 and 120 μm.

4. The process according to claim 1, wherein the release agent composition consists of a sodium phthalate selected from monosodium phthalate or disodium phthalate.

5. The process according to claim 4, wherein the sodium phthalate is selected from disodium orthophthalate, disodium isophthalate and disodium terephthalate.

6. The process according to claim 5, wherein the disodium phthalate is disodium orthophthalate.

\* \* \* \* \*